United States Patent [19]

Mizerak

[11] 4,263,908
[45] Apr. 28, 1981

[54] NASAL CANNULA MASK

[76] Inventor: Vladimir S. Mizerak, R.F.D. 1, Box 367, Springvale, Me. 04083

[21] Appl. No.: 60,723

[22] Filed: Jul. 25, 1979

[51] Int. Cl.³ .............................................. A61M 15/08
[52] U.S. Cl. ........................... 128/205.25; 128/206.23; 128/207.18
[58] Field of Search ....................... 128/205.25, 206.21, 128/206.28, 207.11, 207.18, 206.23

[56] References Cited

U.S. PATENT DOCUMENTS 780,709   1/1905   Craig ............................ 128/207.18 X Primary Examiner—Henry J. Recla
Attorney, Agent, or Firm—William Nitkin

[57] ABSTRACT

Disclosed is a nasal cannula having oral gas delivery means incorporated therein adapted to increase efficiency in providing gas, such as oxygen, to a patient.

3 Claims, 2 Drawing Figures

NASAL CANNULA MASK

BACKGROUND OF THE INVENTION

1. Field of the Invention

The apparatus of this invention resides in the area of respiratory devices for the administration of oxygen or other gases to a patient and more particularly relates to nasal cannula.

2. History of the Prior Art

In recent years the field of respiratory therapy has increased in importance due to greater understanding of the proper administration of oxygen or other gases to patients. Patients requiring oxygen or other gases are often given masks which usually cover the mouth and nose area. Such masks are used only for a short period of time. To provide a more continuous supply of oxygen or other gases to a bedridden patient, nasal cannulae have come into wide use. Such cannulae are usually comprised of a hollow tubular portion open at each end with a pair of hollow nasal extensions communicating with the interior of the hollow tubular portion, adapted to be inserted into the nostrils of the patient. Nasal cannulae are now provided in soft, flexible material so as to be non-irritating to the user and are disposable to avoid cross-contamination between patients of respiratory ailments. The oxygen or other gas is provided to the open ends of the hollow tubular portion by supply tubes coming from a main oxygen or gas supply. The cannulae are held in place by either the supply tubes extending over the ears of the patient or by an elastic band passing around the patient's head.

Frequently patients encounter problems by such nasal cannulae due to many factors such as deviated nasal septums and are unable to receive the proper oxygen or other gas supply through their nostrils. These problems may include the plugging of the upper nostrils due to secretions within the patient or merely due to the fact that the patient breathes through his mouth rather than through his nose. Although as one breaths through the mouth, oxygen is usually taken through the nose due to a venturi effect with a lower air pressure found at the rear of the nasal pharynx. In order to overcome some of these problems, the use of a nasal cannula is discontinued and the full face mask has been used which typically extends over the nose and around the chin of the individual. It has been appreciated by those close to the field of respiratory therapy that such masks, due to their weight, apply pressure on the outside of the patient's nose which although it is a light pressure, is enough to reduce the internal diameter of the air passageways within the nose making breathing through the nose difficult. Also many patients, being anxious, become upset when a mask is placed on them which often contributes to the patient having a suffocating sensation and accompanying panic.

SUMMARY

It is an object of this invention to provide a nasal cannula mask, the use of which does not create any of the problems cited above in the History of the Prior Art and which can be utilized as simply as the apparatus of the prior art and which will be accepted by the patient without upset or discomfort.

It is a further object of this invention to provide an apparatus that is light in weight and which does not put pressure on the nose of the user or contribute in any way to imparting a choking sensation.

The apparatus of this invention provides for a hollow tubular portion being open at each end with a pair of hollow nasal extensions opening into the interior of the hollow tubular portion, said nasal extensions being spaced apart the distance of the nostrils of the patient so as to be able to be inserted therein. Supply tubes may be inserted or bonded to the open ends of the hollow tube. These supply tubes extend to a main gas or oxygen supply. A cup-like mask extends from the hollow supply tube and is adapted to cover over the mouth of the patient, being wider at the mouth and resting on the chin. An oxygen or other gas feed aperture is defined within the front portion of the hollow tubular portion approximately 1.5 times the size of the diameter of one of the hollow openings in a nasal extension. A channel is formed on the upper portion of the mouth mask which is adapted so that said oxygen or other gas feed aperture feeds oxygen or other gas into the channel which subsequently passes into the hollow of the mask around the mouth of the patient. The mask is not adapted to fit in an air-tight relation to the patient's face around the mouth so that the patient may draw air in from around the sides of the mask which air mixes with the oxygen or other gas when the patient inhales. Also oxygen or other gas passes upwards through the nasal extensions into the nostrils of the patient. The mask portion of the apparatus is not adapted to pass below the chin so as to avoid any feelings of confinement by the patient. Further no portion of the mask rests upon the nose which eliminates any pressure thereon. The bottom of the mask is adapted to rest upon the chin of the patient and by its positioning assists in retaining the nasal extensions in their proper relationship to the nostrils so as to avoid their twisting and putting pressure on the portions of the insides of the nostrils which might cause irritation.

The apparatus of this invention can be injection molded in one piece of a soft flexile transparent plastic material such as polyvinylchloride and preferably designed to be disposable after use. It may be held to the patient by the usual mode of the supply tubes extending over the ears of the patient and then down in front of the patient to a main supply of oxygen or other gas. It may also be held in position by an elastic strap member affixed to either side of the apparatus and passed around the head of the user. A plurality of apertures is provided on both sides of the mask to allow for the entry of air therethrough.

DESCRIPTION OF THE PREFERRED EMBODIMENT(S)

Figure 1:
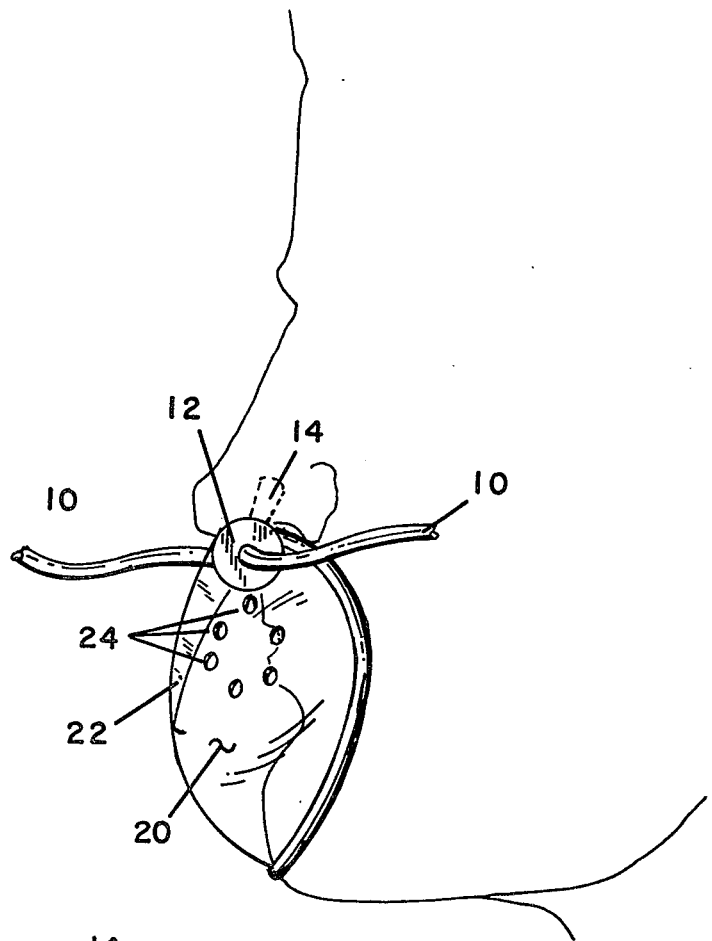
FIG. 1 illustrates a perspective view of the device of this invention.
Figure 2:
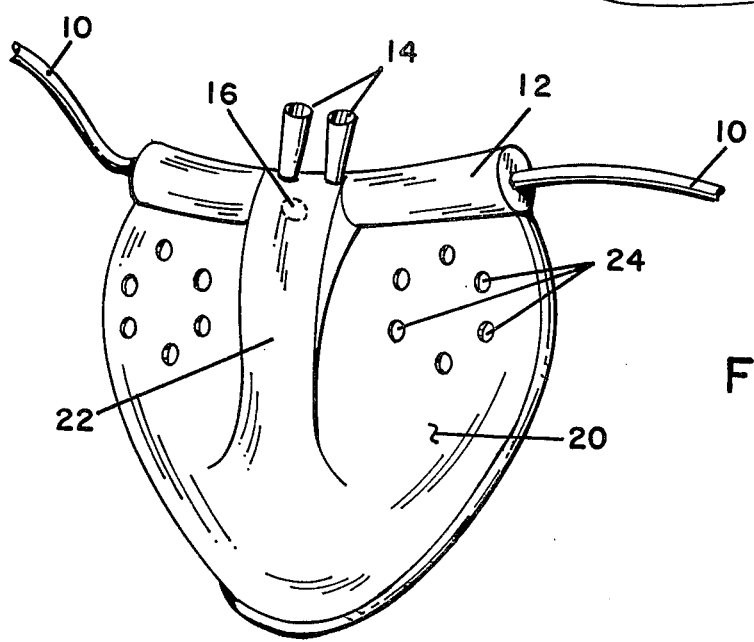
FIG. 2 illustrates a side view of the device of this invention in use on a patient.

The apparatus of this invention is shown in a perspective view in FIG. 1 and in a side view positioned on a patient in FIG. 2. In FIG. 1 supply tubes 10 are illustrated, the ends of which are cutaway, it being understood as in the prior art that they may extend over the ears of the patient ultimately to a gas, hereinafter for convenience referred to as oxygen, main supply. Supply tubes 10 enter on either side into apertures of the wider hollow delivery tube 12. The supply tubes may be frictionally inserted or permanently bonded therein. Extending from an upper portion of hollow delivery tube 12 are a pair of hollow nasal extensions 14 which open into the inside of hollow delivery tube 12. These nasal extensions are spaced apart a distance so that they may be inserted into the nostrils of the user. They may also be flared at the top. At the front portion of the delivery tube at an angle approximately 90 degrees to the apertures of the nasal extensions is defined an oxygen feed aperture 16 which can be of a diameter approximately 1.5 times that of the diameter of the aperture within a single nasal extension. A mouth-covering mask portion 20 is affixed along the hollow delivery tube adapted to pass over the mouth of the patient, the mask being wider than the mouth at its outer perimeter and the base of which is adapted to rest on the patient's chin. Channel 22 is defined within the mask portion of the apparatus covering the oxygen feed aperture 16, feeding such oxygen into the inside of the mouth-covering portion 20 of the apparatus. Channel 22 allows for the oxygen feed aperture 16 to be positioned on the front portion of the hollow delivery tube 12 so that in no way will the oxygen feed aperture 16 be blocked by lip movement of the patient. A series of air apertures 24 may be defined on each side of the mouth mask 20. Air apertures 24 allow outside air to enter the mask for the patient to breathe and are also provided as a safety feature in case oxygen should fail to be provided through the supply tubes. It is expected that the flow of oxygen from the apparatus of this invention would fall between $FiO_2.3$ and $FiO_2.7$. Channel 22 also helps add structural rigidity to mask 20.

The shape of the mouth mask portion is important to the proper functioning of this apparatus and portions of the bottom may be shaped so as to fit around the contours of the chin of the user.

Although the present invention has been described with reference to particular embodiments, it will be apparent to those skilled in the art that variations and modifications can be substituted therefor without departing from the principles and spirit of the invention.

I claim:

1. A nasal cannula of the type adapted to be interconnected to a gas or oxygen supply means with tube delivery means, comprising:

a hollow delivery tube having open ends fo receipt of the gas or oxygen from said supply means;

a pair of hollow nasal extensions extending from an upper portion of said hollow delivery tube, spaced apart a distance adapted for insertion into the user's nostrils;

a gas or oxygen feed aperture defined in the front portion of said hollow delivery tube; and a cup-like mouth mask, the top of which being contiguous with said hollow delivery tube, having a channel defined in an upper portion thereof, said channel adapted to cover said oxygen feed aperture, said mouth mask further adapted to extend downward having sides terminating beyond the user's mouth and its bottom terminating to rest upon the chin of the user wherein said cup-like mouth mask has a plurality of air apertures defined therein.

2. The apparatus of claim 1 wherein said gas or oxygen feed aperture is of a diameter of approximately 1.5 times the diameter of the hollow defined within one of said nasal extensions.

3. A nasal cannula of the type adapted to be interconnected to a gas or oxygen tank supply means with tube delivery means, comprising:

a hollow delivery tube having open ends for receipt of the gas or oxygen from said tank supply means;

a pair of hollow nasal extensions extending from an upper portion of said hollow delivery tube, spaced apart a distance adapted for insertion into the user's nostrils;

a gas or oxygen feed aperture defined in the front portion of said hollow delivery tube in an area between said nasal extensions; and a cup-like mouth mask, the top of which being contiguous with said hollow delivery tube, having an upwardly protruding portion forming a channel defined in an upper central portion thereof, said channel adapted to cover said gas or oxygen feed aperture so that said gas feeds therein into said nasal mask, said mouth mask further adapted to extend downward having sides terminating beyond the sides of the user's mouth and its bottom terminating at a point adapted to rest upon the lower portion of the chin of the user so that the mouth mask does not fit tightly around the user's mouth.

* * * * *